US012736490B2

(12) United States Patent
Hörner

(10) Patent No.: US 12,736,490 B2
(45) Date of Patent: Sep. 15, 2026

(54) METHOD AND SYSTEMS FOR DETERMINING A MEASUREMENT ERROR IN A MEASUREMENT OF HYDROGEN CONCENTRATION

(71) Applicant: Siemens Aktiengesellschaft, Munich (DE)

(72) Inventor: Thomas Hörner, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 18/696,700

(22) PCT Filed: Aug. 23, 2022

(86) PCT No.: PCT/EP2022/073442
§ 371 (c)(1),
(2) Date: Mar. 28, 2024

(87) PCT Pub. No.: WO2023/052004
PCT Pub. Date: Apr. 6, 2023

(65) Prior Publication Data
US 2024/0402108 A1 Dec. 5, 2024

(30) Foreign Application Priority Data
Sep. 30, 2021 (EP) .................................... 21200215

(51) Int. Cl.
*G01N 25/18* (2006.01)
*G01N 33/00* (2006.01)
*G06F 30/20* (2020.01)

(52) U.S. Cl.
CPC ......... *G01N 25/18* (2013.01); *G01N 33/0027* (2013.01); *G06F 30/20* (2020.01)

(58) Field of Classification Search
CPC ..... G01N 25/18; G01N 33/0027; G06F 30/20
See application file for complete search history.

(56) References Cited

U.S. PATENT DOCUMENTS

2011/0158854 A1 6/2011 Horiba
2012/0131987 A1 5/2012 Gellert et al.
(Continued)

FOREIGN PATENT DOCUMENTS

CN 104849374 A 8/2015
CN 105067793 A 11/2015
(Continued)

OTHER PUBLICATIONS

IP_Search_List.*
(Continued)

*Primary Examiner* — Lina Cordero
*Assistant Examiner* — Lynda Dinh
(74) *Attorney, Agent, or Firm* — Henry M. Felereisen LLC

(57) ABSTRACT

A computer-implemented method generates a model for determining a measurement error in a measurement of concentration of hydrogen present in a gas mixture. The gas mixture comprises hydrogen and a non-hydrogen-containing carrier gas mixture. Data for at least two different non-hydrogen-containing carrier gas mixture compositions are provided. Based on the data, different gas mixture compositions are produced, with a different non-hydrogen-containing carrier gas mixture composition and/or different hydrogen content in different gas mixture compositions. Hydrogen concentration measurements are ascertained for the gas mixture compositions, and the hydrogen concentration measurements are used to ascertain measurement errors. A model which maps data for carrier gas mixture compositions and hydrogen concentration measurements onto measurement errors is provided.

12 Claims, 2 Drawing Sheets

(56) References Cited

U.S. PATENT DOCUMENTS

| | | | | |
|---|---|---|---|---|
| 2014/0060152 | A1* | 3/2014 | Probst | G01N 33/005 73/23.41 |
| 2016/0238546 | A1* | 8/2016 | Hill | G01N 33/005 |
| 2016/0363573 | A1 | 12/2016 | Lai et al. | |
| 2020/0254383 | A1* | 8/2020 | Roodbeen | B01D 53/227 |
| 2021/0155856 | A1* | 5/2021 | Jemison | B01D 3/14 |
| 2021/0262996 | A1 | 8/2021 | Kojima et al. | |
| 2021/0339190 | A1* | 11/2021 | Gallucci | C01B 3/50 |
| 2023/0249967 | A1* | 8/2023 | Storms | F17C 1/14 220/586 |

FOREIGN PATENT DOCUMENTS

| | | | | |
|---|---|---|---|---|
| CN | 209952607 | U | * | 1/2020 |
| DE | 102008061158 | B3 | | 4/2010 |
| DE | 100 03 676 | B4 | | 6/2013 |
| DE | 102012004756 | A1 | * | 9/2013 |
| EP | 3454059 | A1 | | 3/2019 |
| EP | ON 110988272 | A | | 4/2020 |
| UA | 19 753 | U | * | 12/2016 |

OTHER PUBLICATIONS

Google_Scholar_Search_List.*

PCT International Search Report and Written Opinion of International Searching Authority mailed Jan. 3, 2023 corresponding to PCT International Application No. PCT/EP2022/073442 filed Aug. 23, 2022.

Jaworski Jacek et al:; "Study of the Effects of Changes in Gas Composition as Well as Ambient and Gas Temperature on Errors of Indications of Thermal Gas Meters"; Oct. 17, 2020; Energies.

* cited by examiner

Process Control System
100
Gas Turbine
101
Measurement Output
Measurement Input
1071
1070
106
Computing Facility
108
2 Model
Data
40
Measuring Chamber
1072
Gas Analysis Device
107
CAN Bus
1074
A/D Output
1075
1073
Power Connection Point
102
Fuel Gas
Mixing Apparatus
103
105
Hydrogen
Control Facility
110
Gas Chromatograph Device
109
Direction of Flow
104
Carrier Gas

METHOD AND SYSTEMS FOR DETERMINING A MEASUREMENT ERROR IN A MEASUREMENT OF HYDROGEN CONCENTRATION

CROSS-REFERENCES TO RELATED APPLICATIONS

This application is the U.S. National Stage of International Application No. PCT/EP2022/073442, filed Aug. 23, 2022, which designated the United States and has been published as International Publication No. WO 2023/052004 A1 and which claims the priority of European Patent Application, Serial No. 21200215.8, filed Sep. 30, 2021, pursuant to 35 U.S.C. 119 (a)-(d).

BACKGROUND OF THE INVENTION

The invention relates to a computer-implemented method for generating a model for determining a measurement error in a measurement of concentration of hydrogen that is contained in a gas mixture, wherein the gas mixture comprises hydrogen and a non-hydrogenous carrier gas mixture.

In addition, the invention relates to a computer program product or a computer program comprising commands that, when the computer program is executed by a computer, cause the computer to execute the aforementioned method.

In addition, the invention relates to a computer-readable data carrier on which the aforementioned computer program product or computer program is stored, and a data carrier signal which transmits the aforementioned computer program product or computer program.

In addition, the invention relates to a method for determining a measurement error in a concentration measurement of hydrogen that is contained in a gas mixture, wherein the gas mixture comprises hydrogen and a non-hydrogenous carrier gas mixture.

The invention further relates to a system for measuring hydrogen concentration comprising a gas analysis facility and a computing facility that is allocated to the gas analysis facility.

For the energy industry, the use of hydrogen (especially from renewable sources) is becoming increasingly interesting. In particular, the application . . . for admixture in fuel gas, for example in natural gas, plays an important role here. The hydrogen-fuel gas mixture can be combusted in a turbine, for example, and converted into electricity and heat. The control of the turbines that are used requires a rapid hydrogen concentration measurement in order to keep the operating point stable.

One possible approach to measuring the hydrogen concentration is a partial pressure measurement. Due to the high thermal conductivity of hydrogen, the partial pressure measurement of hydrogen is often performed by means of thermal conductivity sensors. For this purpose, for example gas analysis devices or field devices that operate according to the principle of thermal conductivity measurement are known. Such devices can operate continuously, for example, and are primarily used for the quantitative determination of $H_2$ or He in binary or quasi-binary gas mixtures.

Other application examples are chlorine-alkali electrolysis (0 . . . 10% $H_2$ in $Cl_2$); metallurgy (steel production and processing); $H_2$ measurement in the LNG (liquified natural gas) process; ammonia synthesis; artificial fertilizer production.

In the simplest case, the measurement takes place using a gas analysis device that operates according to the principle of thermal conductivity measurement in a binary mixture, for example $H_2$ (hydrogen) in $N_2$ (nitrogen) or $H_2$ in $CH_4$ (methane), etc. Any further admixture to the carrier gas worsens the accuracy of the measurement. For use in a fuel gas application (for example natural gas-hydrogen mixture), it is therefore necessary to match the measurement to the existing gas matrix. Since the carrier gas is not isolated, but only in the presence of $H_2$, this is hardly possible. The analyzer (the gas analysis device) must therefore be prepared for all natural gas sources without making complex (and sometimes impossible) adaptations on site.

It is therefore the object of the present invention to provide methods and systems that enable an aforementioned preparation of the analyzer.

SUMMARY OF THE INVENTION

The object is achieved in accordance with the invention with a computer-implemented method mentioned in the introduction in that data is provided regarding at least two different non-hydrogenous carrier gas mixture compositions. The data can be present, for example, in the form of a file on a storage medium, for example on a portable non-volatile storage medium. The data can be provided, for example, on a server in a network, for example on the internet, in a cloud or the like.

Based on the data regarding the at least two different non-hydrogenous carrier gas mixture compositions, different gas mixture compositions are generated or produced (for example automatically, in a computer-aided manner) (for example in the form of tables on a computer). In the different gas mixture compositions, the non-hydrogenous carrier gas mixture composition and/or the hydrogen content or the hydrogen concentration are/is different.

In one embodiment, it can be provided that when generating the different gas mixture compositions, hydrogen is added to each non-hydrogenous carrier gas mixture composition from, for example, approximately 0.0% by volume to, for example, approximately 100.0% by volume. In this way, based on a single carrier gas mixture composition, a plurality of different gas mixture compositions can be generated by changing the ratio between the carrier gas mixture and the hydrogen in the gas mixture. This can be done, for example, by successively, for example in 1% steps, increasing the hydrogen concentration in the gas mixture (and a corresponding reduction in the concentration of the carrier gas mixture). It goes without saying that smaller steps, for example of 0.1%, or larger steps, for example of 2%, can also be selected.

Subsequently, (expected) hydrogen concentration measured values are determined for the gas mixture compositions that are generated. Measuring errors are determined on the basis of the determined hydrogen concentration measured values. This can be done, for example, by comparing the determined hydrogen concentration measured values with the (actual) hydrogen concentrations that are known from the generation of the gas mixture compositions. This establishes a relationship between the carrier gas mixture compositions and hydrogen concentration measured values on the one hand and the (expected) measurement errors on the other.

In a further step, a model is provided (based on the established relationship) that maps or can map data regarding carrier gas mixture compositions and hydrogen concentration measured values to measurement errors. In other words, the model includes relationships between the carrier gas mixture compositions and hydrogen concentration measurements and the (expected) measurement errors that enable the aforementioned mapping.

The model can be based on a linear regression, decision trees (gradient boosted trees) or neural networks. Linear regression is preferably used to establish the relationships between the carrier gas mixture compositions and hydrogen concentration measured values on the one hand and the measurement errors on the other, and thus to generate the model.

The model is thus generated on the basis of the data regarding gas mixture compositions or trained using this data, which is intended for use in a gas analysis device that operates according to the principle of thermal conductivity measurement, and in the case of a real measurement, outputs a corresponding measurement error with which the measured value is afflicted for the measured value and a provided carrier gas mixture composition.

At this point, it should be noted that the different gas mixture compositions can not only be generated virtually, as described above. It can be provided, for example for the purpose of monitoring the method, that the gas mixture compositions are produced in parallel in a laboratory, for example by means of a mixing apparatus that can mix a carrier gas mixture with hydrogen. In this case, the hydrogen concentration measured values can be measured using a gas analysis device that operates according to a thermal conductivity measuring principle, wherein the measuring errors that are determined in the measurement can be compared with the measuring errors that are determined using the model.

In one embodiment, it can therefore be provided that the hydrogen concentration measured values are based on a measurement.

Alternatively or additionally, in one embodiment, it can be provided that the hydrogen concentration measured values are calculated.

In this case it can be expedient if the data comprises a characteristic curve of a gas analysis device that operates according to a thermal conductivity measuring principle, wherein thermal conductivities of the gas mixture compositions are calculated, and the hydrogen concentration measured values are calculated from the (calculated) thermal conductivities on the basis of the characteristic curve.

A computing facility that is suitable for implementing the aforementioned method is also disclosed. For example, the computing facility can have a first interface with which it can receive the data regarding at least two different non-hydrogenous carrier gas mixture compositions. The computing facility can furthermore have a computing unit, for example a processor, and a storage device that is operatively connected to the computing unit, for example a volatile or non-volatile storage device. The storage device is configured, for example, so as to store or buffer the data, wherein the computing unit is configured so as to generate the different gas mixture compositions based on the data, and to determine hydrogen concentration measured values for the different gas mixture compositions, for example on the basis of a characteristic curve that is optionally present in the data. Furthermore, the computing unit is configured so as to determine measurement errors on the basis of the hydrogen concentration measured values, for example by comparison with the actual hydrogen content that has been specified during generation. The computing facility can furthermore have a second interface with which it provides the model. Alternatively or additionally, the computing facility can be configured so as to provide the model via the second interface and to store a copy of the model in its storage device.

In one embodiment, it can be provided that the data comprises information regarding concentration of two, three, four, five or more components that are contained in the carrier gas mixture, preferably for each carrier gas mixture composition.

In one embodiment, it can be provided that each component is selected from the group: methane, carbon dioxide, nitrogen, ethane, propane.

In one embodiment it can be provided that at least one non-hydrogenous carrier gas mixture is a natural gas mixture, preferably all the carrier gas mixtures are natural gas mixtures.

In one embodiment, it can be provided that the carrier gas mixture is a synthetic gas mixture, for example a two-component gas mixture (for example $CO_2$—$CH_4$ mixture).

In one embodiment, it can be provided that a hydrogen concentration measured value is determined for each gas mixture composition, and a measurement error is determined on the basis of the hydrogen concentration measured value and the hydrogen content in the gas mixture composition.

In one embodiment, it can be provided that the data is provided regarding four, twelve, two hundred or more different non-hydrogenous carrier gas mixture compositions. Such data can be based, for example, on the AGA8 table from NIST, or represent the AGA8 table.

In one embodiment, it can be provided that a proportion of the data, preferably 10% to 20%, in particular 15% of the data, is used to validate the model.

In addition, the object is achieved in accordance with the invention by means of the method mentioned in the introduction for determining a measurement error in that data regarding the composition of the non-hydrogenous carrier gas mixture is provided, hydrogen concentration in the gas mixture is measured using a gas analysis device, which operates according to a thermal conductivity measuring principle, in order to obtain a measured value, and a model that is generated, as described above, is applied to the measured value and to the data regarding the composition of the non-hydrogenous carrier gas mixture in order to determine a measurement error for the measured value (in absolute terms in % by volume).

It goes without saying that the model can either have been generated (that is to say before the method is implemented) or is generated first (that is to say while the method is being implemented).

Furthermore, the invention is achieved with a measuring system in accordance with the invention that is mentioned in the introduction in that the gas analysis facility is configured so as to

- measure hydrogen concentration in a gas mixture comprising hydrogen and a non-hydrogenous carrier gas mixture according to a thermal conductivity measuring principle in order to obtain a measured value, wherein the computing facility comprises a model that is generated as described above and is configured so as to
- obtain data regarding the composition of the non-hydrogenous carrier gas mixture, and
- apply the model to the measured value and to the data in order to determine a measurement error for the measured value (in absolute terms in % by volume).

In one embodiment, it can be provided that the computing facility is configured so as to correct the measured value taking into account the measurement error, and preferably to provide the corrected measured value.

In one embodiment, it can be provided that the computing facility is configured so as to transmit the measurement error to the gas analysis facility so that it is automatically taken into account in future measurements.

In one embodiment, it can be provided that the gas analysis facility is configured so as to measure the concentration of at least one component that is contained in the non-hydrogenous carrier gas mixture, and to transmit the measured concentration value to the computing facility or to make it available to the computing facility.

In one embodiment, it can be provided that the gas analysis facility is configured so as to measure the concentration of at least two, three, four, five or more components that are contained in the non-hydrogenous carrier gas mixture, and so as to transmit the measured concentration values to the computing facility or to make them available to the computing facility.

In one embodiment, it can be provided that the gas analysis facility comprises a gas analysis device, which operates according to a thermal conductivity measuring principle, in order to measure hydrogen concentration, and comprises a gas chromatograph device in order to measure the concentration of the at least one component that is contained in the non-hydrogenous carrier gas mixture.

BRIEF DESCRIPTION OF THE DRAWING

Further features, characteristics and advantages of the present invention are provided in the description below with reference to the attached figures. In the drawings.

DETAILED DESCRIPTION OF PREFERRED EMBODIMENTS

Figure 1:
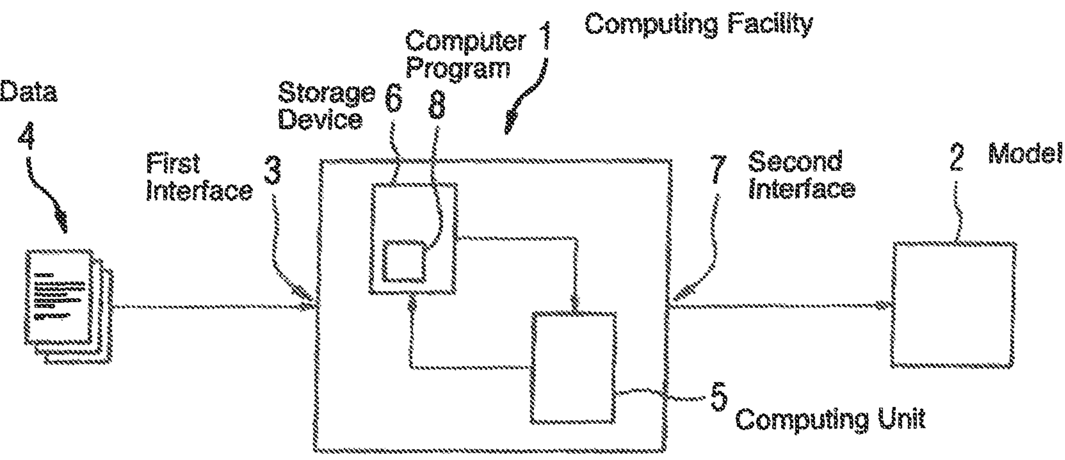
FIG. 1 shows a computing facility.

In the exemplary embodiments and figures, identical or identically acting elements can each be provided with the same reference characters.

Figure 2:
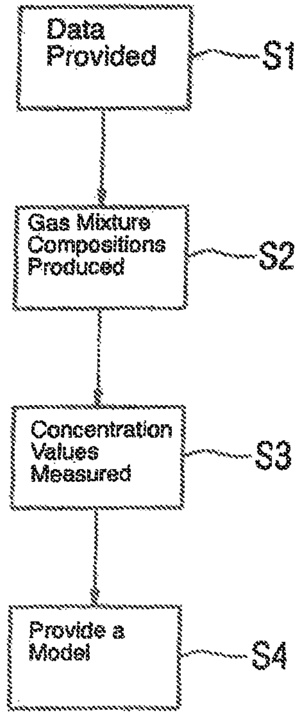
FIG. 2 shows a flowchart of a computer-implemented method.

First, reference is made to FIG. 1 and FIG. 2. FIG. 1 illustrates a computing facility 1 that is suitable for executing a computer-implemented method for generating a model 2 that is illustrated by means of a flowchart in FIG. 2.

For example, the computing facility 1 that is illustrated in FIG. 1 can have a first interface 3 with which it can receive the data 4 regarding at least two different non-hydrogenous carrier gas mixture compositions. The computing facility 1 can furthermore have a computing unit 5, for example a processor, and a storage device 6 that is operatively connected to the computing unit 5, for example a volatile or non-volatile storage device. The storage device 6 is configured, for example, so as to store or buffer the data 4, wherein the computing unit 5 is configured so as to generate the different gas mixture compositions based on the data 4, and to determine hydrogen concentration measured values for the different gas mixture compositions, for example on the basis of a characteristic curve that is optionally present in the data 4. Furthermore, the computing unit 5 is configured so as to calculate measurement errors on the basis of the hydrogen concentration measured values, for example by comparison with the actual hydrogen content that has been specified during generation. This generates a model 2 that can map data regarding carrier gas mixture compositions and hydrogen concentration measured values to measurement errors (corresponding to the hydrogen concentration measured values) on the basis of determined relationships between the carrier gas mixture compositions and hydrogen concentration measured values on the one hand and the (expected) measurement errors on the other hand.

The computing facility 1 can furthermore have a second interface 7 with which it provides the model 2. Alternatively or additionally, the computing facility 1 can be configured so as to provide the model 2 via the second interface 7 and to store a copy of the model 2 in its storage device 6.

FIG. 2 illustrates the computer-implemented method by means of a flowchart. In a step S1, the data 4 is provided regarding at least two different non-hydrogenous carrier gas mixture compositions. The data can be present, for example, in the form of a file on a storage medium, for example on a portable non-volatile storage medium. The data 4 can be provided, for example, on a server (not illustrated) in a network, for example on the internet, in a cloud or the like. For this purpose, the computing facility 1 of FIG. 1 can have a corresponding connection interface.

In a step S2, different gas mixture compositions are produced or generated based on the data 2. In this case, in principle, two sizes can be varied simultaneously or individually. Firstly, the type of carrier gas mixture can be varied. Secondly, the hydrogen content in the gas mixture can be varied.

When generating the different gas mixture compositions, hydrogen can be added to each non-hydrogenous carrier gas mixture composition from, for example, approximately 0.0% by volume to, for example, approximately 100.0% by volume. In this way, based on a single carrier gas mixture composition, a plurality of different gas mixture compositions can be generated by changing the ratio between the carrier gas mixture and the hydrogen in the gas mixture. This can be done, for example, by successively, for example in 1% steps, increasing the hydrogen concentration in the gas mixture (and a corresponding reduction in the concentration of the carrier gas mixture).

In a step S3, (expected) hydrogen concentration measured values are determined for the gas mixture compositions that are generated. Measuring errors are calculated on the basis of the determined hydrogen concentration measured values. Preferably, a hydrogen concentration measured value is determined for each generated gas mixture composition, and the corresponding measurement error is calculated on the basis of this value. This can be done, for example, by comparing the determined hydrogen concentration measured values with the (actual) hydrogen concentrations that are known from the generation of the gas mixture compositions. As a consequence, the model 2 is generated that can map data 4 regarding carrier gas mixture compositions and hydrogen concentration measured values to measurement errors.

In a further step S4, the model 2 is provided.

FIG. 1 shows that the storage device 6 comprises a computer program 8 having commands for executing the method described above.

The hydrogen concentration measured values can be based on a measurement. Alternatively or additionally, the hydrogen concentration measured values can be calculated. For this purpose, a characteristic curve of a gas analysis device that operates according to a thermal conductivity measuring principle can be contained in the data. In this case, thermal conductivities of the gas mixture compositions can be calculated, and the hydrogen concentration measured values can be calculated from the (calculated) thermal conductivities on the basis of the characteristic curve.

It is preferred that the data comprises information regarding concentration of two, three, four, five or more components that are contained in the carrier gas mixture. This information is preferably available for each carrier gas mixture composition. This increases the robustness of the Model 2.

The component can be selected from the group: methane, carbon dioxide, nitrogen, ethane, propane.

In one embodiment it can be provided that at least one non-hydrogenous carrier gas mixture is a natural gas mixture, preferably all the carrier gas mixtures are natural gas mixtures.

The compositions of different natural gases can be presented, for example, in the form of the following TABLE 1:

| Component | min. [% by volume] | typ. [% by volume] | max. [% by volume] | Thermal conductivity [W/m*K] | Thermal conductivity [standardized] |
|---|---|---|---|---|---|
| $CH_4$ | 60 | 88 | 95 | 0.0341 | 1 |
| $C_2H_6$ | 1 | 4 | 14 | 0.02029 | 0.6 |
| $C_3H_8$ | 0.1 | 1.5 | 5 | 0.01682 | 0.49 |
| $CO_2$ | 0.1 | 3 | 11 | 0.01652 | 0.48 |
| $N_2$ | 0.3 | 3.5 | 18 | 0.026 | 0.76 |

In this case, the typical five components (methane, ethane, propane, carbon dioxide, nitrogen) of typical natural gases and their thermal conductivities as well as the thermal conductivities standardized to $CH_4$ are summarized.

Four specific examples EG1, EG2, EG3, EG4 of possible natural gas composition are given in TABLE 2:

| | EG1 | EG2 | EG3 | EG4 |
|---|---|---|---|---|
| $CH_4$ [Vol.-%] | 60.565 | 70.226 | 88.106 | 95.419 |
| $CO_2$ [Vol.-%] | 3.943 | 10.58 | 2.71 | 0.174 |
| $N_2$ [Vol.-%] | 17.582 | 4.348 | 3.172 | 0.25 |
| $C_2H_6$ [Vol.-%] | 13.898 | 10.092 | 0.635 | 4.02 |
| $C_3H_8$ [Vol.-%] | 2.953 | 3.413 | 4.425 | 0.088 |

The data with which the model 2 is generated can also comprise more than four natural gas compositions, for example a plurality thereof, 200 or more.

For example, on the basis of natural gas compositions EG1 to EG4, 404 gas mixture compositions can be generated by adding hydrogen to each of the natural gas compositions EG1 to EG4 step by step, in 1% steps. It goes without saying that smaller steps, for example of 0.1%, can also be selected in order to generate more data points, for example.

Subsequently, a hydrogen concentration measured value can be determined for each of the 404 gas mixture compositions. Thereafter, a measurement error can be determined on the basis of the hydrogen concentration measured value and the hydrogen content in the gas mixture composition.

Figure 3:
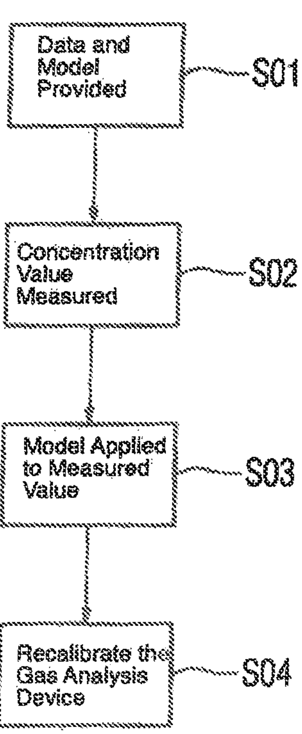
FIG. 3 shows a flowchart of a method for determining a measurement error in a measurement of hydrogen concentration.

FIG. 3 illustrates a flowchart of a method for determining a measurement error in a measurement of hydrogen concentration in a hydrogenous fuel gas mixture.

In a step S01, data is provided regarding the composition of the non-hydrogenous carrier gas mixture and the model 2 that is generated as described above.

In a step S02, hydrogen concentration in the gas mixture is measured using a gas analysis device, which operates according to a thermal conductivity measuring principle, in order to obtain a measured value.

In a step S03, the model 2 is applied to the measured value and to the data regarding the composition of the non-hydrogenous carrier gas mixture in order to determine a measurement error for the measured value (in absolute terms in % by volume).

The method can comprise a further step S04, in which the determined measurement error is used to recalibrate the gas analysis device.

Figure 4:
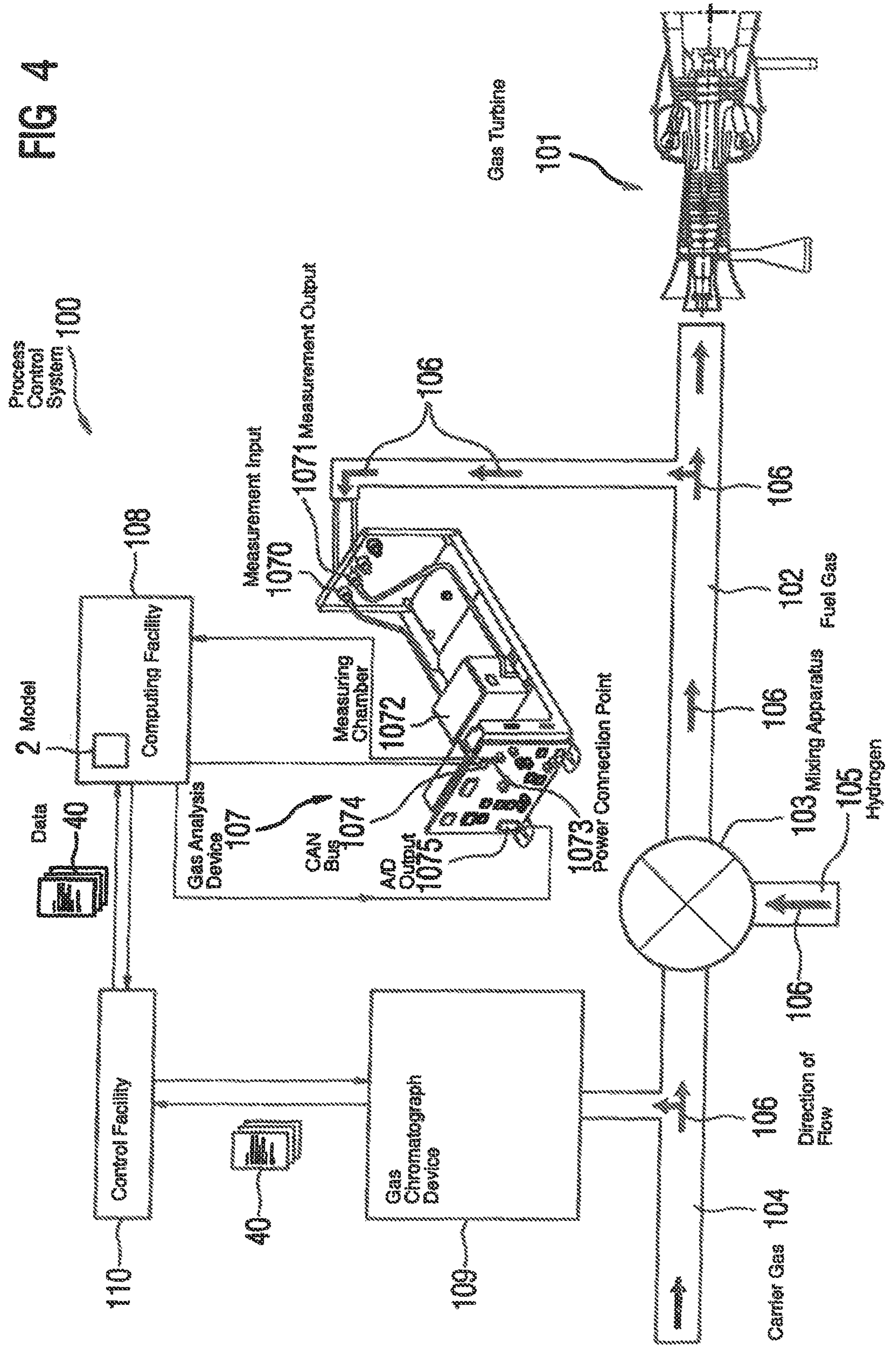
FIG. 4 shows a process control system.

FIG. 4 illustrates a process control system 100 in which a method for determining a measurement error in a measurement of hydrogen concentration in a hydrogenous fuel gas mixture, for example, the method of FIG. 3, can be implemented.

The process control system 100 is configured so as to supply and operate a gas turbine 101 with hydrogenous fuel gas 102.

The fuel gas 102 is prepared in a mixing apparatus 103. A carrier gas 104, for example natural gas or a synthetic gas and hydrogen 105, are fed to the mixing apparatus 103, so that the mixing apparatus 103 can admix hydrogen 105 to the carrier gas 104 in order to generate the fuel gas mixture 102 that is fed to the turbine 101.

A preferred direction of flow of the gases is illustrated by arrows 106.

In addition, the process control system 100 comprises a gas analysis facility, which in the present case has a gas analysis device 107, a computing facility 108 that is allocated to the gas analysis device 107, and a gas chromatograph device 109.

The gas analysis device 107 has a measurement input 1070, through which a measuring gas, for example the fuel gas 102, is introduced into the gas analysis device 107. The gas analysis device 107 also has a measurement output 1071 in order to remove the gas after the measurement.

The gas analysis device 107 furthermore comprises a measuring chamber 1072 that functions according to the principle of thermal conductivity measurement. The measuring principle of the measuring chamber 1072 is based on the different thermal conductivity of gases. The heating of a heated measuring resistor (not shown) that is surrounded by gas is determined by the thermal conductivity of the gas.

In one mode of operation, the measuring chamber 1072 can have a sensor (not shown) that is equipped with a micromechanically produced Si chip, the measuring membrane of which can be provided with thin-film resistors. The resistors that are contained in the membrane are controlled to a constant temperature. For this purpose, a current strength can be used that assumes a certain value depending on the thermal conductivity of the measuring gas. This “raw value” can be further processed electronically and used to calculate the gas concentration. The sensor is characterized in particular by a low T90 time. The sensor is preferably located in a thermostatically controlled stainless steel housing in order to suppress the influence of the ambient temperature. In addition, it can be expedient to only energize the sensor indirectly in order to avoid flow influences. This can be achieved, for example, by mounting the sensor in a hole at the side of the flow channel.

In one mode of operation, it can be provided that the measuring chamber 1072 provides four measuring resistors that are connected to a Wheatstone bridge (not shown). Two of the measuring resistors have measuring gas flowing around them, the other two are surrounded by the reference gas. A constant DC voltage heats the resistors above the temperature of the measuring block 1072. In the case of different thermal conductivity of measuring gas and reference gas, the resistors heat up to an unequal extent due to the converted heating power. A change in the composition of the measuring gas therefore also causes a change in the resistance values. The electrical balance of the measuring bridge is disturbed and a voltage is created in the bridge diagonal. This is a measure of the concentration of the measuring component, here of the hydrogen $H_2$.

For energizing and/or controlling the gas analysis device 107, the gas analysis device 107 can have corresponding interfaces. For power supply, the gas analysis device 107 can have a power connection point 1073. In addition to the power connection point 1073, the gas analysis device 107 can comprise a bus system, preferably a field bus, in particular a CAN bus 1074 (Controller Area Network) and an analogue/digital output 1075.

The computing facility 108 that is allocated to the gas analysis device 107 can additionally be designed as a supply and control facility for the gas analysis device 107 and can be coupled to the aforementioned connections of the gas analysis device 107 (see FIG. 4).

The gas analysis device 107 is configured so as to measure hydrogen concentration in the fuel gas 102 in order to obtain a measured value.

The computing facility 108 comprises a model 2 that is generated, as described above, and is configured so as to obtain data 40 regarding the composition of the carrier gas 104, and to apply the model 2 to the measured value and to the data 40 in order to determine a measurement error (an absolute error in % by volume) for the measured value.

The data 40 regarding the composition of the carrier gas 104 can be based on measurements that are performed on the carrier gas 104 by the gas chromatograph device 109. In this case, the gas chromatograph device 109 is configured so as to measure the concentration of at least one component that is contained in the carrier gas 104. The gas chromatograph device 109 is designed, for example, so as to measure the concentration of methane, ethane, propane, carbon dioxide and nitrogen in the carrier gas 104.

The gas chromatograph device 109 can transmit the measured values to a control facility 110 of the process control system 100. The control facility 110 is designed so as to support the control of the processes that are running in the process control system 100.

The control facility 110 can transmit the data 40 to the computing facility 108 or make it available to the computing facility 108 in some other way.

The computing facility 108 can also be configured so as to correct the measured values that are measured by the gas analysis device 107, taking into account the relevant measurement errors, and to provide the corrected measured values to the control facility 110 so that the control facility 110 can display the corrected measured values, for example.

In addition, the computing facility 108 can be configured so as to control the gas analysis device 107 in accordance with the calculated measurement error, so that the gas analysis device 107 automatically takes the measurement error into account during the next measurement and displays or transmits a corrected measurement value to the computing facility 108. For this purpose, the computing facility 108 can transmit the calculated measurement error to the gas analysis device 107, for example via the field bus 1074.

The gas chromatograph device 109 can perform the measurement, for example, at regular time intervals, for example, at a sampling rate of 180 seconds.

Using the gas analysis device 107, the measurement can be performed much more frequently than with the gas chromatograph device 109. The measurement is preferably performed at a sampling rate of 5 seconds.

Although the invention has been illustrated and described in more detail by exemplary embodiments, the invention is not limited by the disclosed examples. Variations thereof can be derived by the person skilled in the art without departing the scope of protection of the invention as defined by the following claims. In particular, the features disclosed in connection with the systems described here can expediently be used for developing the methods described here, and vice versa.

The invention claimed is:

1. A method for measuring a gas mixture, the method comprising:

providing data regarding at least two different non-hydrogenous carrier gas mixture compositions to a computing facility of a process control system;

generating different gas mixture compositions based on the data regarding the at least two different non-hydrogenous carrier gas mixture compositions, wherein the different gas mixture compositions have different non-hydrogenous carrier gas mixture compositions and/or hydrogen contents;

determining hydrogen concentration measured values for the different gas mixture compositions;

determining measurement errors based on the hydrogen concentration measured values;

generating a model that maps data regarding the non-hydrogenous carrier gas mixture compositions and the hydrogen concentration measured values to the measurement errors for the different gas mixture compositions;

providing the model to the computing facility of the process control system;

providing a non-hydrogenous carrier gas mixture in a gas flow;

measuring a composition of the non-hydrogenous carrier gas mixture in the gas flow with a gas chromatograph device;

transmitting data regarding the measured composition of the non-hydrogenous carrier gas mixture in the gas flow from the gas chromatograph device to a control facility of the process control system;

feeding the non-hydrogenous carrier gas mixture in the gas flow and hydrogen in another gas flow to a mixing apparatus to admix the non-hydrogenous carrier gas mixture and the hydrogen to produce a fuel gas mixture;

measuring a hydrogen concentration in the fuel gas mixture with a gas analysis device, which operates according to a thermal conductivity measuring principle, in order to obtain a measured value of the hydrogen concentration of the fuel gas mixture;

transmitting the measured value of the hydrogen concentration of the fuel gas mixture to the computing facility of the process control system;

applying the model, with the computing facility of the process control system, to the measured value of the hydrogen concentration of the fuel gas mixture and to the data regarding the measured composition of the non-hydrogenous carrier gas mixture in order to determine a measurement error for the measured value of the hydrogen concentration of the fuel gas mixture;

correcting with the computing facility of the process control system the measured value of the hydrogen concentration of the fuel gas mixture that is measured by the gas analysis device, taking into account the determined measurement error for the measured value of the hydrogen concentration of the fuel gas mixture; and controlling the gas analysis device with the computing facility of the process control system in accordance with the determined measurement error for the measured value of the hydrogen concentration of the fuel gas mixture, so that the gas analysis device automatically takes the determined measurement error for the measured value of the hydrogen concentration of the fuel gas mixture into account during a next measurement with the gas analysis device.

2. The method of claim 1, wherein the data regarding the at least two different non-hydrogenous carrier gas mixture compositions comprises information regarding concentration of two, three, four, five or more components that are contained in the non-hydrogenous carrier gas mixture.

3. The method of claim 2, wherein each component is selected from the group consisting of: methane, carbon dioxide, nitrogen, ethane, and propane.

4. The method of claim 1, wherein the different gas mixture compositions comprise the hydrogen and two or more non-hydrogenous natural gas mixtures.

5. The method of claim 1, wherein, when generating the different gas mixture compositions, the hydrogen is added to each non-hydrogenous carrier gas mixture composition from 0.0% by volume to 100.0% by volume.

6. The method of claim 1, wherein the hydrogen concentration measured values are determined for each gas mixture composition, and the measurement errors are determined based on the hydrogen concentration measured values and the hydrogen content in the each gas mixture composition.

7. The method of claim 6, wherein the hydrogen concentration measured values are measured with the gas analysis device.

8. The method of claim 6, wherein the hydrogen concentration measured values are calculated.

9. The method of claim 8, wherein the data regarding the at least two different non-hydrogenous carrier gas mixture compositions comprises a characteristic curve of the gas analysis device that operates according to the thermal conductivity measuring principle, wherein thermal conductivities of the gas mixture compositions are calculated, and the hydrogen concentration measured values are calculated from the thermal conductivities based on the characteristic curve.

10. The method of claim 1, wherein the data regarding the at least two different non-hydrogenous carrier gas mixture compositions is provided regarding four, twelve, 200 or more different non-hydrogenous carrier gas mixture compositions.

11. A non-transitory computer program product storing a computer program having commands that, when the computer program is being executed by a computer, cause the computer to implement the method as set forth in claim 1.

12. A process control system comprising:

a control facility;

a mixing apparatus;

a gas chromatograph device;

a gas analysis device; and a computing facility configured to:

receive data regarding at least two different non-hydrogenous carrier gas mixture compositions;

generate different gas mixture compositions based on the data regarding the at least two different non-hydrogenous carrier gas mixture compositions, wherein the different gas mixture compositions have different non-hydrogenous carrier gas mixture compositions and/or a hydrogen contents;

determine hydrogen concentration measured values for the different gas mixture compositions;

determine measurement errors based on the hydrogen concentration measured values;

generate a model that maps data regarding the non-hydrogenous carrier gas mixture compositions and the hydrogen concentration measured values to the measurement errors for the different gas mixture compositions;

provide a non-hydrogenous carrier gas mixture in a gas flow;

measure a composition of the non-hydrogenous carrier gas mixture in the gas flow with the gas chromatograph device;

transmit data regarding the measured composition of the non-hydrogenous carrier gas mixture in the gas flow from the gas chromatograph device to a control facility of the process control system;

feed the non-hydrogenous carrier gas mixture in the gas flow and hydrogen in another gas flow to a mixing apparatus to admix the non-hydrogenous carrier gas mixture and the hydrogen to produce a fuel gas mixture;

measure a hydrogen concentration in the fuel gas mixture with the gas analysis device, which operates according to a thermal conductivity measuring principle, in order to obtain a measured value of the hydrogen concentration of the fuel gas mixture;

receive the measured value of the hydrogen concentration of the fuel gas mixture;

apply the model to the measured value of the hydrogen concentration of the fuel gas mixture and to the data regarding the measured composition of the non-hydrogenous carrier gas mixture in order to determine a measurement error for the measured value of the hydrogen concentration of the fuel gas mixture;

correct the measured value of the hydrogen concentration of the fuel gas mixture that is measured by the gas analysis device, taking into account the determined measurement error for the measured value of the hydrogen concentration of the fuel gas mixture; and controlling the gas analysis device in accordance with the determined measurement error for the measured value of the hydrogen concentration of the fuel gas mixture, so that the gas analysis device automatically takes the determined measurement error for the measured value of the hydrogen concentration of the fuel gas mixture into account during a next measurement with the gas analysis device.

* * * * *